(12) United States Patent
Boles et al.

(10) Patent No.: US 8,691,554 B2
(45) Date of Patent: Apr. 8, 2014

(54) MODIFIED YEAST CONSUMING L-ARABINOSE

(75) Inventors: Eckhard Boles, Dreieich (DE); Jessica Becker, Dusseldof (DE)

(73) Assignee: Scandinavian Technology Group AB, Lund (SE)

( * ) Notice: Subject to any disclaimer, the term of this patent is extended or adjusted under 35 U.S.C. 154(b) by 842 days.

(21) Appl. No.: 12/325,630

(22) Filed: Dec. 1, 2008

(65) Prior Publication Data

US 2009/0215138 A1    Aug. 27, 2009

Related U.S. Application Data

(63) Continuation of application No. 11/498,002, filed on Aug. 2, 2006, now abandoned, which is a continuation of application No. 10/983,951, filed on Nov. 8, 2004, now abandoned, which is a continuation of application No. PCT/SE03/00749, filed on May 7, 2003.

(30) Foreign Application Priority Data

May 8, 2002  (SE) ..................... 0201428
Jul. 4, 2002  (SE) ..................... 0202090

(51) Int. Cl.
  *C12N 1/00*    (2006.01)
  *C12P 1/00*    (2006.01)
  *C12P 1/02*    (2006.01)
  *C12P 19/00*   (2006.01)

(52) U.S. Cl.
  USPC ............. 435/254.1; 435/171; 435/41; 435/72

(58) Field of Classification Search
  USPC ........ 435/254.1, 171, 41, 72, 97, 183, 254.41
  See application file for complete search history.

(56) References Cited

FOREIGN PATENT DOCUMENTS

WO    9850524      11/1998
WO    WO 98/50524  11/1998

OTHER PUBLICATIONS

Rudinger, J., "Characteristics of the amino acids as components of a peptide hormone sequence", in Peptide Hormones, University Park Press: Baltimore, MD, pp. 1-7, 1976.*
Romanos et al., Foreign gene expression in Yeast:a Review. 1992 by John Wiley and Sons Ltd, Yeast, vol. 8:423-488.*
"Expression of *E. coli* araBAD Operon Encoding Enzymes for Metabolizing L-arabinose in *Saccharomyces cerevisiae*," Sedlak et al., *Enzyme and Microbial Technology*, vol. 28 (2001).
"Development of an Arabinose-Fermenting *Zymomonas mobilis* Strain by Metabolic Pathway Engineering," Deanda et al., *Applied an Environmental Microbiology*, vol. 62, n. 12 (1996).
Notice of Opposition filed by DSM IP Assests B.V. against EP1499708 mailed Mar. 2006.
Response to the Notice of Opposition regarding EP1499708 filed by the applicant mailed on Jun. 13, 2007.
Final response to Observations and Amendments regarding EP1499708 mailed on Jan. 2, 2008.
Summons to attend oral proceedings regarding European Patent1499708 mailed on Mar. 16, 2010.
Voet, Donald; "Chemical Evolution"; 1990 John Wiley & Sons; Sections 6-3; pp. 125-128.
Sedlak et al., "Expression of *E. coli* araBAD operon encoding enzymes for metabolizing L-arabinose in *Saccharomyces cerevisiae*"; Enzyne and Microbial Technology; Laboratory of Renewable Resources Engineering; Purdue University, 1295 Potter Center, West Lafayette, IN; pp. 16-24, 2001.
Kimchi-Sarfaty et al., "A "Silent" Polymorphism in the MDR1 Gene Changes Substrate Specificity"; www.sciencemag.org; Science; vol. 315, Jan. 2007; pp. 525-528.
Johansson et al., "Xylulokinase Overexpression in Two Strains of *Saccharomyces cerevisiae* Also Expressing Xylose Reductase and Xylitol Dehydrogenase and Its Effect on Fermentation of Xylose and Lignocellulosic Hydrolysate"; Department of Applied Microbiology, Lund University, 221 00 Lund, Sweden; pp. 4249-4255, vol. 67, 2001.
Cummings et al., "Genomic BLAST: custom-defined virtual databases for complete and unfinished genomes"; National Center for Biotechnology Information, National Library of Medicine, National Institutes of Health, Bethesda, MD 20894; FEMC S Microbiology Letters 216 (2002); pp. 133-138.
"BLAST with microbial genomes (358 bacterial/ 26 archaeal/ 93 eukaryotic genomes tree)"; genomic BLAST; NCBI; pp. 1-11; http://www.ncbi.nlm.nih.gov/sutils/genom_table.cgi; Dec. 30, 2005.
Mims et al., "Bacterial causes of diarrhea"; Medic Microbiology; Third Edition; pp. 279-282, 2004.
Becker et al., "A Modified *Saccharomyces cerevisiae* Strain That Consumes L-Arabinose and Produces Ethanol"; Applied and Environmental Microbiology, Jul. 2003; American Society for Microbiology; vol. 69, No. 7; pp. 4144-4150.

* cited by examiner

*Primary Examiner* — Maria Leavitt
(74) *Attorney, Agent, or Firm* — Gesmer Updegrove LLP

(57) ABSTRACT

The present invention relates to a method for producing a L-arabinose utilizing yeast strain for the production of ethanol, whereby a yeast strain is modified by introducing and expressing araA gene (L-arabinose isomerase), araB gene (L-ribulokinase $D^{121}$-N) and araD gene (L-ribulose-5-P 4-epimerase) and carrying additional mutations in its genome or overexpressing a TAL1 (transaldolase) gene, enabling it to consume L-arabinose, to use it as the only carbon source, and to produce ethanol, as well as a method for producing ethanol using such a modified strain.

4 Claims, No Drawings

MODIFIED YEAST CONSUMING L-ARABINOSE

PRIORITY INFORMATION

This application is a continuation of now abandoned U.S. patent application Ser. No. 11/498,002, filed on Aug. 2, 2006, which was a continuation of now abandoned U.S. patent application Ser. No. 10/983,951 filed on Nov. 8, 2004 which is a continuation of PCT Application No. PCT/SE03/00749, filed on May 7, 2003, which claims priority to Swedish Patent Application Nos. 0201428-0 and 0202090-7, filed May 8, 2002 and Jul. 4, 2002 respectively, all of which are incorporated herein by reference in their entirety.

DESCRIPTION

1. Technical Field

The present invention relates to a modified yeast strain, preferably a *Saccharomyces cerevisiae*, consuming L-arabinose while producing ethanol, as well as a method for producing ethanol.

2. Background of the Invention

Fuel ethanol is considered as a suitable alternative to fossil fuels and it can be produced from plant biomass, which is a low cost and renewable resource available in large amounts. For this reason cellulose biomass, which includes agricultural residues, paper wastes, wood chips, etc., is an ideal abundantly available source of sugars for the fermentation to ethanol. For example when glucose is produced from cereals, hemi-cellulose-containing by-products mainly consisting of the pentose sugars arabinose and xylose (arabinoxylan) are generated. These are presently used as a low price cattle feed. But this resource could be utilized in a more profitable way if it would be integrated into existing starch processing which yields ethanol and starch derivatives.

In the context of conversion of hemi-cellulose sugars, fermentability of L-arabinose becomes important. The approximation is often made that hydrolysates generated by dilute acid pretreatment, contain only D-xylose because this is the most abundant hemi-cellulose sugar. Resulting from this most studies on conversion of hemi-cellulose hydrolysates focus on the conversion of D-xylose. However hemi-cellulose as a heteropolysaccharide contains pentosans and hexosans. Although xylan is the dominant pentosan and glucomannan is the dominant hexosan the levels of arabinan are significant in some biomass materials. In particular arabinan levels are significant in herbaceous species where it represents up to 10-20% of total non-glucan carbohydrate. Microbial biocatalysts selected to develop or ferment hydrolysates derived from materials with high arabinan content must therefore exhibit the ability to ferment L-arabinose as well as xylose and preferably also other sugars to ethanol.

Many types of yeast, especially *Saccharomyces cerevisiae* and related species have traditionally been used for fermenting glucose based feedstocks to ethanol by anaerobic fermentation because they are the safest and most effective microorganisms for fermenting sugars to ethanol. But these superior glucose fermenting yeasts are unable to ferment xylose and L-arabinose and are also unable to use these pentose sugars for growth. A few other yeast species such as *Pichia stipitis* and *Candida shehatae* can ferment xylose to ethanol; however, they are not as effective as *Saccharomyces* for fermentation of glucose and have a relatively low ethanol tolerance. Thus, they are not suitable for large scale industrial production of ethanol from biomass. Some yeast can utilize L-arabinose for growth but no yeast can ferment it to commercial amounts of ethanol. Unlike yeasts and fungi, most bacteria, including *E. coli* and *Bacillus subtilis*, can utilize L-arabinose for aerobic growth and are also able to ferment it to various products including ethanol.

Sedlak & Ho, Enzyme Microb Technol 28, (2001) pp. 16-24 discloses an expression of *E. coli* araBAD operon encoding enzymes for metabolizing L-arabinose in *Saccharomyces cerevisiae*. The strain hereby expresses araA, araB and araD, but is incapable of producing any ethanol.

SUMMARY OF THE INVENTION

It has now been possible to solve this problem, whereby a new *Saccharomyces cerevisiae* yeast strain able to consume L-arabinose, has been created, and to produce ethanol.

DETAILED DESCRIPTION OF THE PRESENT INVENTION

It has now surprisingly been found possible to overcome the problem of having a yeast consuming L-arabinose by means of the present invention by obtaining a method for producing a L-arabinose utilizing yeast strain for the production of ethanol, which method is characterized in that a yeast strain is modified by introducing and expressing *B. subtilis* araA gene (L-arabinose isomerase, *E. coli* araB gene (L-ribulokinase) and *E. coli* araD gene (L-ribulose-5-P 4-epimerase), and carrying additional mutations in its genome or overexpressing the *S. cerevisiae* TAL1 (transaldolase) gene, enabling it to consume L-arabinose, and to produce ethanol.

The invention will be described more in detail in the following by reference to a number of experiments described explaining the nature of the invention.

The application further encompasses the *Saccharomyces cerevisiae* strain JBY25-4M (DSM 15560) and *Saccharomyces cerevisiae* strain JBY24-3T (DSM 15559) which were deposited at DSMZ Deutsche Sammlung von Mikroorganismen and Zellkulturen GmbH at Mascheroder Weg 1b, 38124 Braunschweig, Germany on Apr. 4, 2003 under the terms of the Budapest Convention.

First, the *E. coli* genes araA (L-arabinose isomerase), araB (L-ribulokinase) and araD (L-ribulose-5-P 4-epimerase) have been cloned and overexpressed behind the strong HXT7promoter fragment on multicopy vectors in *S. cerevisiae* CEN.PK-strains. Whereas araA did not produce any L-arabinose isomerase activity in the yeast transformants, araB overexpression produced up to 0.7 U/mg protein L-ribulokinase activity and araD produced up to 0.13 U/mg protein L-ribulose-5-P 4-epimerase activity. Transformation of CEN.PK2-1C with all three constructs together did not allow the transformants to grow on L-arabinose medium. It has been shown that the yeast galactose permease (Gal2) is able to transport L-arabinose [J. Bacteriol. 103, 671-678 (1970)]. Simultaneous overexpression of GAL2 behind the ADH1 promoter together with the bacterial L-arabinose metabolising genes did also not allow the transformants to grow on L-arabinose medium.

Second, cloning and overexpression of the *Bacillus subtilis* araA gene behind the strong HXT7 promoter fragment on multicopy vectors in the *S. cerevisiae* CEN.PK2-1C strain resulted in an active protein in yeast, which produced L-arabinose isomerase activity in the order of at least some mU/mg protein. Similarly, overexpression of the *Mycobacterium smegmatis* araA gene behind the strong HXT7 promoter fragment on a multicopy vector in the *S. cerevisiae* CEN.PK2-1C strain produced L-arabinose isomerase activity.

Then, transformants expressing the *B. subtilis* araA gene together with the *E. coli* genes araB and araD as well as the yeast GAL2 gene were incubated in liquid media (synthetic complete or synthetic complete/0.1% yeast extract/0.2% peptone) with L-arabinose as the sole carbon source for several weeks. After 4-5 days of incubation the transformants started to grow slowly in these media, in contrast to a strain containing only four empty vectors. Whenever the cells reached an $OD_{600}$ of 3-4, they were inoculated in fresh medium at an $OD_{600}$ of 0.3, and grown further. Growth became faster after 10 days. These observations indicate the occurrence of spontaneous suppressor mutations enabling the cells to use L-arabinose more efficiently. Otherwise, the cells might become somehow adapted to the use of L-arabinose.

To distinguish between suppressor mutations or an adaptation process, the mutant transformants were grown on glucose medium and then shifted again on arabinose medium. They started to grow on arabinose medium with only a short lag-phase indicating that indeed they contain specific mutations enabling the cells to grow on arabinose. The activities of all three heterologous enzymes were measured in crude extracts of the original and the mutant transformants. Whereas the activities of L-ribulose-5-P 4-epimerase and L-arabinose isomerase were similar in both strains, the L-ribulokinase activity was strongly reduced in the mutant transformants.

When the mutant transformants were selected for loss of their plasmids they were no longer able to grow on arabinose. The plasmids were re-isolated and amplified in *E. coli*. The re-isolated plasmids were transformed into a CEN.PK2-1C wild-type strain. When growth on arabinose of these new transformants was compared to the original mutant transformants, the lag-phase on arabinose medium was significantly prolonged indicating that additional genomic mutations had occurred in the mutant transformants enabling them to grow efficiently on arabinose. Different combinations of original and re-isolated plasmids were transformed into the mutant JBY25 strain. It turned out that replacing the re-isolated GAL2, araD and araA plasmids by the corresponding original plasmid did only slightly affect the ability to grow on arabinose. However, replacing the re-isolated araB (L-ribulokinase) plasmid by the corresponding original plasmid resulted in strongly reduced growth on arabinose.

When the complete re-isolated L-ribulokinase gene was sequenced it showed one mutation, which leads to an exchange of amino acid 121 Asp for an Asn in the conserved sugar kinase domain of the kinase. Determination of the kinetics of the mutant enzyme revealed that its Km value for L-ribulose was increased and the Vmax was decreased.

Growth experiment with the wild-type and mutant kinases expressed from centromeric plasmids in strain JBY25 together with the re-isolated isomerase and epimerase plasmids have also been performed. In case of the mutant kinase this centromeric plasmid did not confer good growth on L-arabinose to the transformants. But the transformants carrying the wild-type kinase on a centromeric plasmid showed better growth then those transformed with the overexpressed kinase. This is another indication that the reduced activity of the kinase is important for better growth on L-arabinose.

To find out whether all four plasmids carrying the *Bacillus subtilis* L-arabinose isomerase, the *E. coli* L-ribulokinase and L-ribulose 5-P 4-epimerase and the yeast Gal2 galactose permease, respectively, are necessary for growth on L-arabinose, the mutant strain was transformed with different combinations of re-isolated and empty plasmids (without any gene for L-arabinose metabolism). Transformants lacking the L-arabinose isomerase, the L-ribulokinase of the L-ribulose 5-P 4-epimerase but transformed with the other three re-isolated plasmids did not show any growth on L-arabinose indicating that these genes are absolutely necessary for the utilization of L-arabinose. Transformants lacking the overexpressed galactose permease are able to grown on L-arabinose medium, but with slightly decreased growth rates as compared to the mutant strain containing all four re-isolated plasmids, indicating that overexpression of a transporter is not necessary for growth on L-arabinose but can improve it.

To test whether only one or more mutations in the genomes of the CEN.PK2-1C wild-type strain enable the transformants to grow on L-arabinose, and whether these mutation(s) are recessive or dominant, the mutant strain and also the wild-type strain, each transformed with the four plasmids for L-arabinose metabolism were crossed with a haploid wild-type strain. Afterwards, growth on L-arabinose was investigated. The diploid mutant strain exhibited faster growth on L-arabinose than the diploid control strain. But the diploid mutant strain did not grow as well as the haploid mutant strain transformed with the four plasmids. The diploid mutant strain was sporulated and terade analysis was performed. The results indicate that there is more than one mutation in the genomes of the strain with at least one being dominant and another one being recessive.

Moreover, overexpression of *S. cerevisiae* TAL1 (transaldolase) together with *B. subtilis* araA (L-arabinose isomerase), mutant *E. coli* araB (L-ribulokinase) and *E. coli* araD (L-ribulose-5-P 4-epimerase) resulted in growth on L-arabinose already in the CEN.PK2-1C wild-type strain.

Ethanol production was determined with the JBY25 mutant strain transformed with the four re-isolated plasmids and incubated in a growth medium with 20 g/L L-arabinose. Under oxygen-limiting conditions at a culture $OD_{600nm}=15$-20, ethanol production rates reached up to 0.06 g ethanol/g dry weight and hour.

We have now demonstrated that it is possible to transfer the method for producing an L-arabinose utilizing yeast strain to other *Saccharomyces cerevisiae* strains that are different from the CEN.PK strains.

We have used the W303 *S. cerevisiae* strain that is not related to the CEN.PK strains, and have transformed this strain with the plasmids expressing *B. subtilis* araA gene (L-arabinose isomerase), the mutant *E. coli* araB gene with reduced activity (L-ribulokinase), *E. coli* araD gene (L-ribulose-5-P 4-epimerase) and *S. cerevisiae* TAL1 (transaldolase) gene.

The transformants could grow on a defined medium with L-arabinose as the sole carbon source, although very slowly. Then, cells were incubated in liquid medium (synthetic complete/0.1% yeast extract/0.2% peptone) with L-arabinose as the sole carbon source for several days. After 4-5 days of incubation the transformants started to grow faster in this medium, in contrast to a W303 strain containing only four empty vectors. Whenever the cells reach an $OD_{600}$ of 3-4, they were inoculated in fresh medium at an $OD_{600}$ of 0.3, and grown further. Finally, after 20 days this resulted in a strain able to grown on L-arabinose medium much more faster, and able to ferment L-arabinose to ethanol.

The invention is a modified yeast strain expressing the bacterial *B. subtilis* araA gene (La-arabinose isomerase), *E. coli* mutant araB gene (L-ribulokinase $D^{121}$-N) and *E. coli* araD gene (L-ribulose-5-P 4-epimerase), and carrying additional mutations in its genome or overexpressing the *S. cerevisiae* TAL1 (transaldolase) gene, enabling it to consume L-arabinose, to use it as the only carbon source, and to produce ethanol.

Normally the growth medium will contain about 20 g of L-arabinose/L. However, growth and production of ethanol will occur between 2 and 200 g/L. There is no need for further sugars, and thus L-arabinose can be used alone. It is possible that co-consumption of xylose and arabinose could work, but this has not been determined so far.

The invention claimed is:

1. A method for the production of ethanol by fermenting an L-arabinose utilizing *Saccharomyces cerevisiae* strain JBY25-4M, DSM15560, in a growth medium containing L-arabinose comprising providing a growth medium containing L-arabinose and adding the *Saccharomyces cerevisiae* strain JBY25-4M, DSM15560, to the medium and fermenting the *Saccharomyces cerevisiae* strain JBY25-4M, DSM15560, in said growth medium containing L-arabinose for the production of ethanol.

2. A method for the production of ethanol by fermenting an L-arabinose utilizing *Saccharomyces cerevisiae* strain JBY24-3T, DSM15559, in a growth medium containing L-arabinose comprising providing a growth medium containing L-arabinose and adding the *Saccharomyces cerevisiae* strain JBY24-3T, DSM15559, to the medium and fermenting the *Saccharomyces cerevisiae* strain JBY24-3T, DSM15559, in said growth medium containing L-arabinose for the production of ethanol.

3. The method according to claim 1, wherein the amount of L-arabinose of the growth medium is 2 to 200 g/l.

4. The method according to claim 2, wherein the amount of L-arabinose of the growth medium is 2 to 200 g/l.

* * * * *